(12) United States Patent
RamosMedina et al.

(10) Patent No.: US 9,084,701 B2
(45) Date of Patent: Jul. 21, 2015

(54) ABSORBENT ARTICLES WITH HOOK AND LOOP FASTENING SYSTEMS

(75) Inventors: Nayda Liz RamosMedina, Cincinnati, OH (US); Michael Timothy Looney, Blue Ash, OH (US); Arman Ashraf, Mason, OH (US); Mark James Kline, Okeana, OH (US); Thomas Alexander Horn, Hofheim (DE); Thierry J. Marche, La Chapelle Basse Mer (FR); Olivier J. Blanc, St Mars du désert (FR)

(73) Assignee: The Procter & Gamble Company, Cincinnati, OH (US)

( * ) Notice: Subject to any disclaimer, the term of this patent is extended or adjusted under 35 U.S.C. 154(b) by 247 days.

(21) Appl. No.: 13/293,188

(22) Filed: Nov. 10, 2011

(65) Prior Publication Data

US 2013/0123738 A1    May 16, 2013

(51) Int. Cl.
*A61F 13/62*    (2006.01)
*A61F 13/56*    (2006.01)
*A44B 18/00*    (2006.01)

(52) U.S. Cl.
CPC ........... *A61F 13/625* (2013.01); *A44B 18/0015* (2013.01); *A61F 13/5622* (2013.01); *A61F 13/62* (2013.01); *A61F 13/622* (2013.01);
(Continued)

(58) Field of Classification Search
CPC ................ Y10T 24/27; Y10T 24/2708; Y10T 428/24008; Y10T 428/24017; A61F 13/5622; A61F 13/62; A61F 13/622; A61F 13/625; A61F 13/627; A44B 18/0015
USPC .............. 604/391; 24/442, 450, 452; 428/100
See application file for complete search history.

(56) References Cited

U.S. PATENT DOCUMENTS 3,138,841 A    6/1964  Naimer
3,192,589 A    7/1965  Pearson
(Continued)

FOREIGN PATENT DOCUMENTS

EP          0276970 A2      8/1988
WO      WO 02/060294        8/2002
(Continued)

OTHER PUBLICATIONS

International Search Report, PCT/US2012/064337, mailed Jan. 28, 2013, 12 pages.
(Continued)

*Primary Examiner* — Tan-Uyen (Jackie) T Ho
*Assistant Examiner* — Kathryn E Ditmer
(74) *Attorney, Agent, or Firm* — Andrew J. Mueller; Andrew A Paul; Charles R. Ware (57) ABSTRACT

A disposable wearable absorbent article having a hook and loop fastening system that comprises a nonwoven female fastening material and a male fastening material with a plurality of bidirectional micro-sized hooks, each having a cap and at least one arm. The height of each hook and cap may be defined relative to the overall thickness of the female fastening material. Caps may have a vertical engagement effective area that has: (a) at least two sides that are substantially parallel; (b) a width-to-thickness aspect ratio from 1 to 2; and (c) an area from 40,000 to 120,000 $\mu^2$. Caps may have an overall recessed width and a deepest recessed depth that is defined relative to the overall fiber cross-sectional dimension.

44 Claims, 7 Drawing Sheets

(52) U.S. Cl.
CPC ............. *Y10T 24/27* (2015.01); *Y10T 24/2708* (2015.01); *Y10T 428/24017* (2015.01)

(56) References Cited

U.S. PATENT DOCUMENTS

| | | | |
|---|---|---|---|
| 3,266,113 A | 8/1966 | Flanagan, Jr. | |
| 3,408,705 A | 11/1968 | Kayser et al. | |
| 3,557,413 A | 1/1971 | Engle | |
| 3,594,863 A | 7/1971 | Erb | |
| 3,594,865 A | 7/1971 | Erb | |
| 3,718,725 A | 2/1973 | Hamano | |
| 3,762,000 A | 10/1973 | Menzin et al. | |
| 4,001,366 A | 1/1977 | Brumlik | |
| 4,056,593 A | 11/1977 | De Navas Albareda | |
| 4,189,809 A | 2/1980 | Sotos | |
| 4,290,174 A | 9/1981 | Kalleberg | |
| 4,338,652 A | 7/1982 | Romanczuk et al. | |
| 4,454,183 A | 6/1984 | Wollman | |
| 4,894,060 A | 1/1990 | Nestegard | |
| 4,984,339 A * | 1/1991 | Provost et al. | 24/452 |
| 5,032,122 A | 7/1991 | Noel et al. | |
| 5,077,870 A | 1/1992 | Melbye et al. | |
| 5,135,740 A | 8/1992 | Katz et al. | |
| 5,326,612 A | 7/1994 | Goulait | |
| 5,339,499 A * | 8/1994 | Kennedy et al. | 24/452 |
| 5,595,567 A | 1/1997 | King et al. | |
| 5,607,635 A | 3/1997 | Melbye et al. | |
| 5,624,427 A | 4/1997 | Bergman et al. | |
| 5,679,302 A | 10/1997 | Miller et al. | |
| 5,792,411 A | 8/1998 | Morris et al. | |
| 5,845,375 A | 12/1998 | Miller et al. | |
| 5,879,604 A | 3/1999 | Melbye et al. | |
| 5,962,102 A * | 10/1999 | Sheffield et al. | 428/92 |
| 6,000,106 A | 12/1999 | Kampfer et al. | |
| 6,039,911 A | 3/2000 | Miller et al. | |
| 6,054,091 A | 4/2000 | Miller et al. | |
| 6,132,600 A | 10/2000 | Marchesseault et al. | |
| 6,206,679 B1 | 3/2001 | Provost et al. | |
| 6,209,177 B1 | 4/2001 | Murasaki | |
| 6,248,419 B1 | 6/2001 | Kennedy et al. | |
| 6,357,088 B2 | 3/2002 | Provost et al. | |
| 6,481,063 B2 | 11/2002 | Shepard et al. | |
| 6,484,371 B1 | 11/2002 | Romanko et al. | |
| 6,526,633 B2 | 3/2003 | Provost et al. | |
| 6,558,602 B1 | 5/2003 | Melbye et al. | |
| 6,635,212 B1 | 10/2003 | Melbye et al. | |
| 6,637,079 B1 | 10/2003 | Goulait et al. | |
| 6,660,202 B2 | 12/2003 | Shepard et al. | |
| 6,728,998 B2 | 5/2004 | Wang et al. | |
| 6,737,147 B2 | 5/2004 | Kennedy et al. | |
| 6,770,065 B1 | 8/2004 | Sasaki et al. | |
| 6,814,912 B2 | 11/2004 | Ausen et al. | |
| 6,869,554 B2 | 3/2005 | Provost et al. | |
| 6,982,055 B2 | 1/2006 | Seth et al. | |
| 7,007,351 B2 | 3/2006 | Ausen et al. | |
| 7,014,906 B2 | 3/2006 | Tuman et al. | |
| 7,032,278 B2 | 4/2006 | Kurtz, Jr. | |
| 7,048,818 B2 | 5/2006 | Krantz et al. | |
| 7,052,636 B2 | 5/2006 | Ausen et al. | |
| 7,052,638 B2 | 5/2006 | Clarner et al. | |
| 7,067,185 B2 | 6/2006 | Ausen et al. | |
| 7,172,008 B2 | 2/2007 | Vanbenschoten et al. | |
| 7,182,992 B2 | 2/2007 | Ausen et al. | |
| 7,185,401 B2 | 3/2007 | Ausen et al. | |
| 7,188,396 B2 | 3/2007 | Melbye et al. | |
| 7,516,524 B2 | 4/2009 | Provost et al. | |
| 7,520,033 B2 | 4/2009 | Clarner | |
| 2003/0106188 A1 * | 6/2003 | Armela et al. | 24/451 |
| 2003/0145440 A1 | 8/2003 | Ausen et al. | |
| 2004/0068848 A1 | 4/2004 | Ausen et al. | |
| 2006/0154019 A1 * | 7/2006 | Cheng | 428/100 |
| 2010/0298796 A1 | 11/2010 | Horn et al. | |

FOREIGN PATENT DOCUMENTS

| | | |
|---|---|---|
| WO | WO-2011-098251 A1 | 8/2011 |
| WO | WO-2011-098252 A1 | 8/2011 |

OTHER PUBLICATIONS

International Search Report mailed Feb. 6, 2012 (11 pages).

* cited by examiner

ABSORBENT ARTICLES WITH HOOK AND LOOP FASTENING SYSTEMS

FIELD

The present disclosure relates to articles with hook and loop fastening systems, and more particularly relates to wearable absorbent articles with hook and loop fastening systems having a female fastening material made of a fibrous material and a male fastening material with hooks configured for the fibrous material.

BACKGROUND

A hook and loop fastening system can be used to fasten things together. For example, a hook and loop fastening system can be used to fasten a disposable wearable absorbent article around a wearer. In a hook and loop fastening system, a male fastening material includes hooks and a female fastening material includes loops. The male fastening material is configured to releasably engage the female fastening material. In some hook and loop fastening systems, the female fastening material is a fibrous material. However, if the hooks of a male fastening material are not configured for the loops of a fibrous material, then few loops are captured and retained by the hooks, and the male fastening material cannot be used with the fibrous material to form a reliable hook and loop fastening system.

SUMMARY

Hook and loop fastening systems of the present disclosure have a female fastening material made of a fibrous material and a male fastening material having hooks configured for the fibrous material. The hooks can have an overall hook height that is sized in relation to the overall thickness of the fibrous material. The hooks can have a vertical engagement effective area with a defined size and aspect ratio. The hooks can also have an overall cap height that is sized in relation to the overall thickness of the fibrous material and/or in relation to the overall fiber cross-sectional dimension of fibers in the fibrous material. The hooks can further have arms with undersides that include recessed portions sized in relation to the overall fiber cross-sectional dimension of fibers in the fibrous material. Since the hooks of the male fastening material are configured for the loops of the fibrous material, during fastening a sufficient number of loops are effectively captured and retained by the hooks, and the male fastening material can be used to form a reliable hook and loop fastening system. Particular embodiments are described herein in the Detailed Description. These hook and loop systems can be used with various articles. For example, these hook and loop fastening systems can be used to fasten disposable wearable absorbent articles around wearers.

DETAILED DESCRIPTION

Hook and loop fastening systems of the present disclosure have a female fastening material made of a fibrous material and a male fastening material having hooks configured for the fibrous material. The hooks can have features that are sized and/or shaped in relation to the overall thickness of the fibrous material and/or in relation to the overall fiber cross-sectional dimension of fibers in the fibrous material. Since the hooks of the male fastening material are configured for the loops of the fibrous material, during fastening a sufficient number of loops are effectively captured and retained by the hooks, and the male fastening material can be used to form a reliable hook and loop fastening system. These hook and loop systems can be used with various articles.

Throughout the present disclosure, hook and loop fastening systems are described for use with wearable absorbent articles. Wearable absorbent articles are used to absorb and contain bodily waste (such as urine, menses, and feces) received from a wearer. Wearable absorbent articles include diapers (for people of all ages), training pants, incontinence undergarments, feminine sanitary pads, etc.

However, the hook and loop fastening systems of the present disclosure are not limited to such articles; such systems can be used with all kinds of articles. For example, hook and loop fastening systems of the present disclosure can be used to hold disposable cleaning pads in place on a cleaning device. As another example, hook and loop fastening systems of the present disclosure can also be used to fasten disposable garments, medical wraps, and other articles, as will be understood by one of ordinary skill in the art.

Figure 1A:
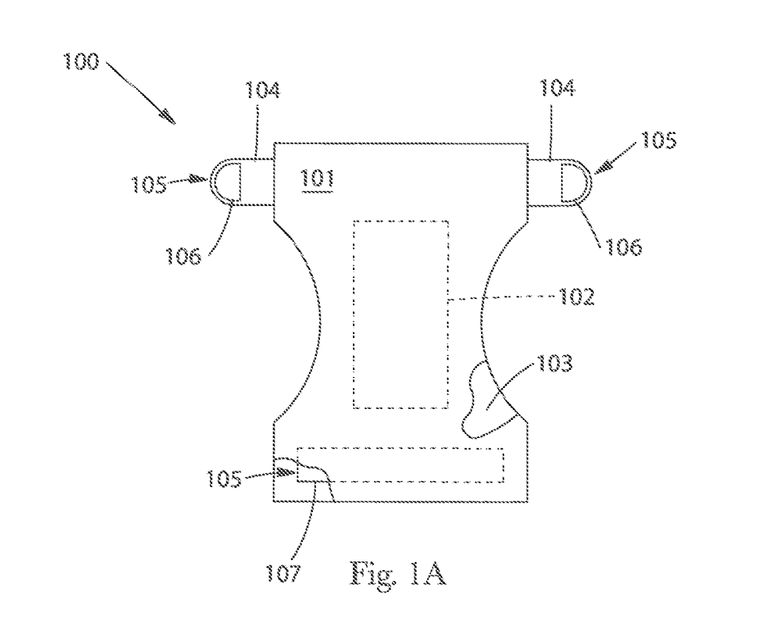
FIG. 1A is a top view of an inside of a front-fastenable disposable wearable absorbent article laid out flat.

FIG. 1A is a top view of an inside of a front-fastenable disposable wearable absorbent article 100 laid out flat. The article 100 includes a topsheet 101, an outer cover 103, and an absorbent core 102 disposed between the topsheet 101 and the outer cover 103. In various embodiments, part, parts, or all of the outer cover 103 can be inextensible, or inelastically extensible, or elastically extensible, either laterally, or longitudinally, or both laterally and longitudinally. A portion of the topsheet 101 is illustrated as cut-away to show a portion of the outer cover 103. In the embodiment of FIG. 1A, the outer cover 103 has a fibrous outer surface. The article 100 includes side ears 104 attached to a back of the article 100. The article 100 also includes a hook and loop fastening system 105 for fastening the article 100 around a wearer. The hook and loop fastening system 105 includes a female fastening material 107 and pieces of a male fastening material 106. In the embodiment of FIG. 1A, the female fastening material 107 is a landing zone disposed on the outside of the front of the outer cover 103. A portion of the topsheet 101 is illustrated as cut-away to show a portion of the female fastening material 107. A piece of the male fastening material 106 is disposed on each of the side ears 104. In various embodiments, part, parts, or all of either or both of the side ears 104 can be inextensible, or inelastically extensible, or elastically extensible, either laterally, or longitudinally, or both laterally and longitudinally.

The disposable wearable absorbent article 100 can also be configured in various alternative embodiments. Any of the single pieces of fastening material on the article 100 may be replaced with two or more pieces of the fastening material. Any piece of either of the fastening materials may be integral with one or more other materials, layers, structures, or features, disclosed herein or known in the art, or to a chassis of the article 100. As an example, the male fastening material 106 may be integral with the side ear 104; that is, one or more materials of the side ear 104 may form the male fastening material. As another example, the female fastening material 107 may be integral with the outer cover 103; that is, one or more materials of the outer cover 103 may form the female fastening material.

The male fastening material 106 and the female fastening material 107 may be located in different locations; for example, the male fastening material 106 may be disposed on the outside of the front of the outer cover 103 and one or more pieces of the female fastening material 107 may be disposed on each of the side ears 104. The front-fastenable disposable wearable absorbent article 100 can alternatively be configured as a rear-fastenable disposable wearable absorbent article. A front-fastenable or rear-fastenable disposable wearable absorbent article can alternatively be configured to fasten only on one side. The front-fastenable disposable wearable absorbent article 100 can alternatively be configured with side margins, instead of side ears. The disposable wearable absorbent article 100 can alternatively be configured as a reusable wearable absorbent article, with a removable absorbent insert.

A disposable absorbent article is configured to be disposed of after a single use (e.g., not intended to be reused, restored, or laundered). Examples of disposable absorbent articles include disposable diapers as well as disposable incontinence undergarments. Some absorbent articles are reusable. A reusable absorbent article is configured to be partly or wholly used more than once. In some embodiments, a reusable absorbent article may be configured such that part or all of the absorbent article is wear-resistant to laundering or fully launderable. An example of a reusable absorbent article is a diaper with a washable outer cover. In other embodiments, a reusable absorbent article may not be configured to be launderable.

Also, the disposable wearable absorbent article 100, or any of its alternative embodiments, can be configured with another fastening system that includes one or more pieces of either or both of the male fastening material 106 and the female fastening material 107, including any of their alternative embodiments. For example, the disposable wearable absorbent article 100 can include a fastening system for attaching a removable absorbent insert to a chassis of the article 100. As another example, the disposable wearable absorbent article 100 can include a fastening system for attaching one or more materials, layers, structures, or features, disclosed herein or known in the art, to each other or to a chassis of the article 100.

Part, parts, or all of the female fastening material 107 can be configured in any manner disclosed herein or known in the art, including any workable combination of structures or features. For example, the female fastening material 107 can be configured in the same way as the female fastening material 310 of FIG. 3A, including any alternative embodiments. Part, parts, or all of either or both pieces of the male fastening material 106 can be configured in any manner disclosed herein or known in the art, including any workable combination of structures or features. For example, the male fastening material 106 can be configured in the same way as the male fastening material 420 of FIG. 4, including any alternative embodiments.

Part, parts, or all of the fastening system 105 can be configured in any manner disclosed herein or known in the art, including any workable combination of structures or features. As an example, the fastening system 105 can include the male fastening material 106, as described above, but may include, a female fastening material that is configured differently than the female fastening material 107, and instead is configured as some other female fastening material known in the art. As another example, the fastening system 105 can include the female fastening material 107, as described above, but may include, a male fastening material that is configured differently than the male fastening material 106, and instead is configured as some other male fastening material known in the art.

Part, parts, or all of the front-fastenable disposable wearable absorbent article 100 can be configured in any manner disclosed herein or known in the art, including any workable combination of structures or features, including any alternative embodiments.

Figure 1B:
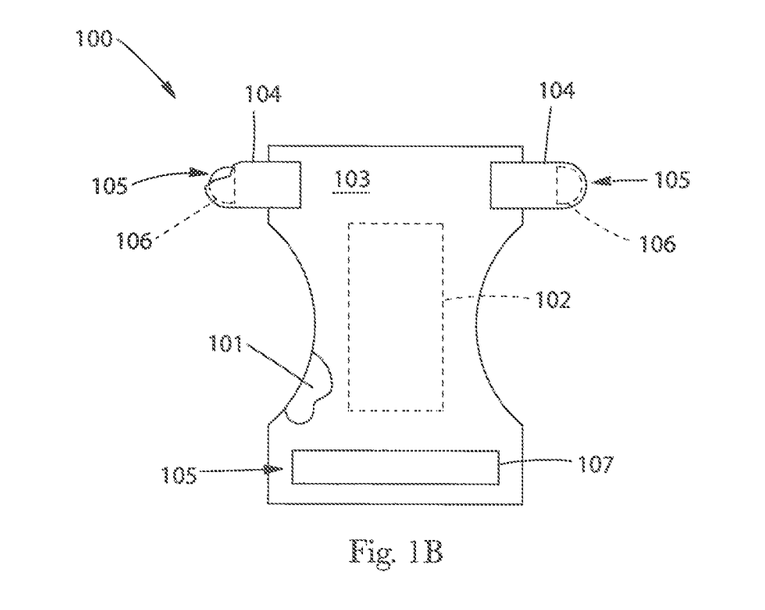
FIG. 1B is a top view of an outside of the front-fastenable disposable wearable absorbent article of FIG. 1A, laid out flat.

FIG. 1B is a top view of an outside of the front-fastenable disposable wearable absorbent article 100 of FIG. 1A, laid out flat. A portion of the outer cover 103 is illustrated as cut-away to show a portion of the topsheet 101. A portion of one of the side ears 104 is also illustrated as cut-away to show a portion of the male fastening material 106.

Any embodiment of the front-fastenable disposable wearable absorbent article 100 of FIGS. 1A and 1B can be manufactured with the fastening system 105 unfastened, or partially fastened, or fully fastened. Any embodiment of the front-fastenable disposable wearable absorbent article 100 of FIGS. 1A and 1B can be sold with the fastening system 105 unfastened, or partially fastened, or fully fastened. When an embodiment of the front-fastenable disposable wearable absorbent article 100 of FIGS. 1A and 1B is sold as unfastened or partially fastened, the consumer, user, or caregiver can fully fasten the article around a wearer.

Figure 2A:
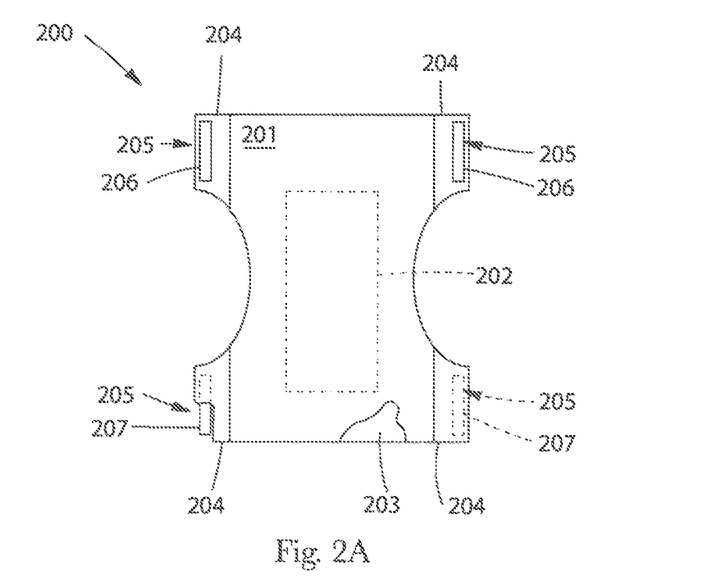
FIG. 2A is a top view of an inside of a side-fastenable disposable wearable absorbent article laid out flat.

FIG. 2A is a top view of an inside of a side-fastenable disposable wearable absorbent article 200 laid out flat. The article 200 includes a topsheet 201, an outer cover 203, and an absorbent core 202 disposed between the topsheet 201 and the outer cover 203. In various embodiments, part, parts, or all of the outer cover 103 can be inextensible, or inelastically extensible, or elastically extensible, either laterally, or longitudinally, or both laterally and longitudinally. A portion of the topsheet 201 is illustrated as cut-away to show a portion of the outer cover 203. In the embodiment of FIG. 2A, the outer cover 203 has a fibrous outer surface. The article 200 includes side panels 204 attached to both sides of the front of the article 200 and to both sides of the back of the article 200. The article 200 also includes a hook and loop fastening system 205 for fastening the article 200 around a wearer. The hook and loop fastening system 205 includes pieces of a male fastening material 206 and pieces of a female fastening material 207. In the embodiment of FIG. 2A, a piece of the male fastening material 206 is disposed on the inside of each of the side ears 204 in the back of the article 200, and a piece of the female fastening material 207 is disposed on the outside of each of the side ears 204 in the front of the article 200. A portion of one of the side panels 204 is illustrated as cut-away to show a portion of one of the pieces of the female fastening material 207. In various embodiments, part, parts, or all of either or both of the side panels 204 can be inextensible, or inelastically extensible, or elastically extensible, either laterally, or longitudinally, or both laterally and longitudinally.

The disposable wearable absorbent article 200 can also be configured in various alternative embodiments. Any of the single pieces of fastening material on the article 200 may be replaced with two or more pieces of the fastening material. Any piece of either of the fastening materials may be integral with one or more other materials, layers, structures, or features, disclosed herein or known in the art, or to a chassis of the article 200. As examples, the male fastening material 206 and/or the female fastening material 207 may be integral with the side ears 204; that is, one or more materials of the side ear 204 may form the fastening material.

The male fastening material 206 and the female fastening material 207 may be located in different locations. For example, the male fastening material 206 may be disposed on either or both of the side panels 204 in the front of the article and the female fastening material 207 may be disposed on either or both of the side panels 204 in the back of the article 200. As another example, one or more pieces of the male fastening material 206 may be disposed on the outside of one or more of the side panels 204 while one or more pieces of the female fastening material 207 may be disposed on the inside of one or more of the side panels 204.

The side-fastenable disposable wearable absorbent article 200 can alternatively be configured with side panels only in the front, or only in the back, or only on one side. The side-fastenable disposable wearable absorbent article 200 can alternatively be configured with side margins, instead of side panels. The side-fastenable disposable wearable absorbent article 200 can alternatively be configured without discrete side panels, but with one or more pieces of fastening material disposed on either or both sides of the chassis in the front or the back of the article 200. The disposable wearable absorbent article 200 can alternatively be configured as a reusable wearable absorbent article, with a removable absorbent insert.

Also, the disposable wearable absorbent article 200, or any of its alternative embodiments, can be configured with another fastening system that includes one or more pieces of either or both of the male fastening material 106 and the female fastening material 107, including any of their alternative embodiments. For example, the disposable wearable absorbent article 200 can include a fastening system for attaching a removable absorbent insert to a chassis of the article 200. As another example, the disposable wearable absorbent article 200 can include a fastening system for attaching one or more materials, layers, structures, or features, disclosed herein or known in the art, to each other or to a chassis of the article 200.

Part, parts, or all of either piece or both pieces of the female fastening material 207 can be configured in any manner disclosed herein or known in the art, including any workable combination of structures or features. For example, the female fastening material 207 can be configured in the same way as the female fastening material 310 of FIG. 3A, including any alternative embodiments. Part, parts, or all of either piece or both pieces of the male fastening material 206 can be configured in any manner disclosed herein or known in the art, including any workable combination of structures or features. For example, the male fastening material 206 can be configured in the same way as the male fastening material 420 of FIG. 4, including any alternative embodiments.

Part, parts, or all of the side-fastenable disposable wearable absorbent article 200 can be configured in any manner disclosed herein or known in the art, including any workable combination of structures or features, including any alternative embodiments.

Figure 2B:
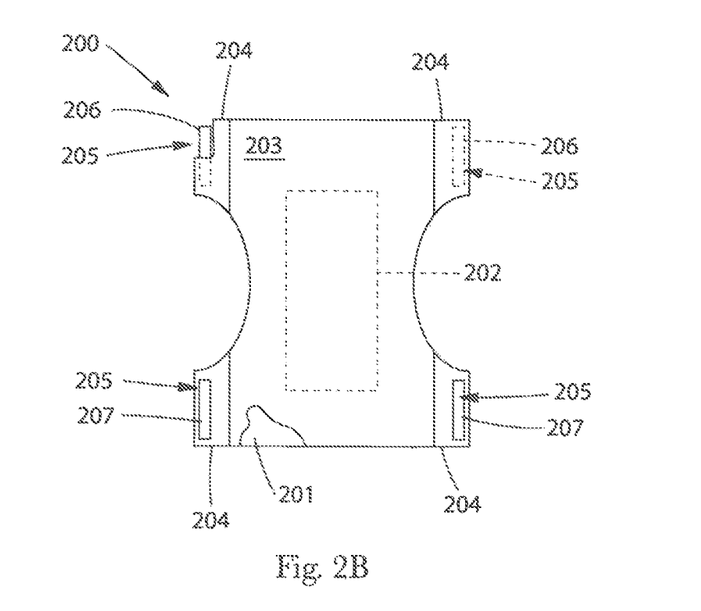
FIG. 2B is a top view of an outside of the side-fastenable disposable wearable absorbent article of FIG. 2A, laid out flat.

FIG. 2B is a top view of an outside of the side-fastenable disposable wearable absorbent article 200 of FIG. 2A, laid out flat. A portion of the outer cover 203 is illustrated as cut-away to show a portion of the topsheet 201. A portion of one of the side panels 204 is also illustrated as cut-away to show a portion of one of the pieces of the male fastening material 206.

Any embodiment of the side-fastenable disposable wearable absorbent article 200 of FIGS. 2A and 2B can be manufactured with the fastening system 205 unfastened, or partially fastened, or fully fastened. Any embodiment of the front-fastenable disposable wearable absorbent article 200 of FIGS. 2A and 2B can be sold with the fastening system 205 unfastened, or partially fastened, or fully fastened. When an embodiment of the front-fastenable disposable wearable absorbent article 200 of FIGS. 2A and 2B is sold as unfastened or partially fastened, the consumer, user, or caregiver can fully fasten the article around a wearer.

Any of the wearable absorbent articles disclosed herein can be configured with various structures and/or features, as will be understood by one of skill in the art. As an example, a wearable absorbent article can include any of the following layers (from the skin of the wearer outward): a topsheet, an acquisition layer, a distribution layer, a core cover, a storage layer, a dusting layer, and/or an outer cover, and/or one or more other layers known in the art, with each layer configured in any way known in the art. A layer in a wearable absorbent article can be formed from one or more of various materials, such as fibrous web, film, paper, tissue, etc. and laminates made from any combination of any of these, in any way known in the art. Each layer in a wearable absorbent article can be configured with various appropriate properties, such as hydrophilicity, hydrophobicity, liquid permeability, liquid impermeability, porosity, breathability, extensibility, elasticity, opacity, transparency, strength, and/or softness, etc. in any way known in the art.

An absorbent core can include one or more absorbent materials, such as superabsorbent materials and/or natural materials (which may or may not be processed into various forms). In various embodiments, part, parts, or all of a topsheet, an acquisition layer, a distribution layer, a core cover, a storage layer, and/or a dusting layer can include various coatings and/or additives such as lotions, perfumes, and sensates for various purposes, such as antimicrobial action, deodorizing, promoting skin health, etc. An absorbent core can be configured as a bucket-shaped absorbent core, as part of a removable absorbent core, as part of a replaceable absorbent core, as part of an absorbent core assembly, etc.

Also, a disposable wearable absorbent article can include any of the following: a waist band, a finished waist edge, a leg band, a finished leg opening, an outer leg cuff, an inner leg cuff, and/or a barrier leg cuff. Further, a disposable wearable absorbent article can include any of the following: a feces containment compartment, one or more wetness indicators, disposal tapes, etc. Still further, various structures and features of as disposable wearable absorbent article can include artwork, passive graphics, active graphics, indicia, and product information, in any combination known in the art.

It is further contemplated that any of the embodiments of the present disclosure can be configured as described in PCT published Application No. WO 2013-068779 A1, entitled "Hook Fastener," filed Nov. 10, 2011, by Aplix, S.A. (of Paris, France) in the name of Thierry Marche, et al., which is hereby incorporated by reference. Specifically, any of the male fastening materials (including any hook configurations), any of the female fastening materials, and any of the hook and loop fastening systems disclosed herein can be configured as described therein.

Figure 3A:
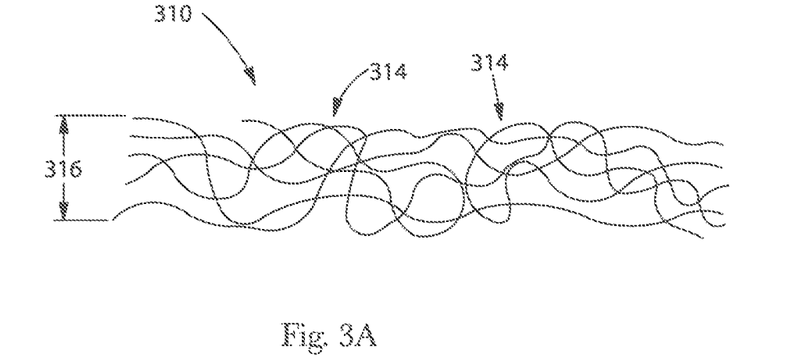
FIG. 3A is an enlarged side view of a portion of a female fastening material.

FIG. 3A is an enlarged side view of a portion of a female fastening material 310. The female fastening material 310 is a fibrous material with an overall thickness 316. In the embodiment of FIG. 3A, the female fastening material 310 is a nonwoven material. The nonwoven material has a plurality of fibers 314. Each of the fibers 314 has an overall fiber cross-sectional dimension.

In various embodiments, the female fastening material 310 can be any fibrous material or any other material suitable for releasably engaging hooks of a male fastening material, as disclosed herein or as known in the art. As an example, the fibrous outer surface of an outer cover of a disposable wearable absorbent article can be used as a female fastening material. In some embodiments, the female fastening material 310 can be disposed on as layer of material that acts as a substrate.

Fibrous materials can be made from one or more of various types of fibers, such as animal fibers, plant fibers, mineral fibers, synthetic fibers, etc. Fibrous materials can include short fiber, long fibers, continuous fibers, and/or fibers of varying lengths or combinations of any of these. In some cases, a fibrous material can include another material, can be joined to another material, or can be incorporated into another material. Fibrous materials can take many forms, such as fabrics, textiles, and composites. Examples of fabrics include fibrous textiles (woven or knitted fabrics), felts, nonwovens, and others. An example of a fibrous composite is a composite material with polymeric fibers.

Throughout the present disclosure, nonwoven materials are used to describe and illustrate various embodiments. However, it is contemplated that embodiments of the present disclosure are not limited to nonwoven materials, but can be similarly applied to a wide variety of fibrous materials, such as those described above and others, as will be understood by one of skill in the art. As used herein, the term "nonwoven material" refers to a sheet-like structure (e.g. web) of fibers (sometimes referred to as filaments) that are interlaid in a non-uniform, irregular, or random manner. A nonwoven material can be a single layer structure or a multiple layer structure. Each layer in a nonwoven material can include one kind of fibers or two or more kinds of fibers, with each kind of fiber configured in any way described herein or known in the art. A nonwoven material can also be joined to another material, such as a film, to form a laminate. A nonwoven web can be bonded to provide integrity to the web and/or to attach the nonwoven web to another material.

A nonwoven material can be made from various natural and/or synthetic materials. Exemplary natural materials include cellulosic fibers, such as cotton, jute, pulp, and the like; and also can include reprocessed cellulosic fibers like rayon or viscose. Natural fibers for a nonwoven material can be prepared using various processes such as carding. Notably, a nonwoven material can be made from fibers made from renewable materials. Exemplary synthetic materials include but are not limited to synthetic thermoplastic polymers that are known to form fibers, which include, but are not limited to, polyolefins (e.g. polyethylene, polypropylene, polybutylene and the like); polyamides (e.g. nylon 6, nylon 6/6, nylon 10, nylon 12 and the like); polyesters (e.g. polyethylene terephthalate, polybutylene terephthalate, polylactic acid and the like); polycarbonate; polystyrene; thermoplastic elastomers; vinyl polymers; polyurethane; as well as blends and copolymers thereof, and any additives or processing aids known in the art. Any of these materials can be used to form one or more mono-component fibers, and any combination of any of these materials can be used to form one or more of any kind of multi-component fibers in any configuration.

Fibers of a relatively short length (e.g. 40 mm or less) are typically manufactured into a nonwoven using processes like drylaying (e.g. carding or airlaying) or wetlaying. Continuous fibers or filaments can be spun out of molten thermoplastics or chemical solutions and formed into a web using spunlaying/spunbonding, meltblowing, or electrospinning by example. Another process for forming a nonwoven is film fibrillation. These processes can also be combined to form composite or layered fabric structures.

Each layer in a fibrous material or particular fibers in a fibrous material can be configured with various appropriate properties, such as air permeability, porosity, breathability, extensibility, elasticity, opacity, transparency, strength, and/or softness, etc. in any way known in the art.

A fibrous material used as a female fastening material can also be configured with any bond pattern and any printing known in the art. For example, a female fastening material can be configured with bond patterns and/or printing as described in published US patent application 20100298796, entitled "Wearable Absorbent Articles With Bonded And Printed Fibrous Materials," filed May 20, 2010 by The Procter & Gamble Company, under the name of Horn, et al.

As an example, a fibrous material used as a female fastening material in a hook and loop fastening system, can be a nonwoven material made from bicomponent fibers, with components being: a propylene-ethylene copolymer (80%) and a propylene homo-polymer (20%), arranged in side-by-side configuration.

Following are further examples of female fastening materials suitable for use in a hook and loop fastening system. One example is a nonwoven available from 3M Company, St. Paul, Minn., USA under the trade designation EBL. Another example comprises a number of shaped engaging elements projecting from a woven backing such as the commercially available material designated Guilford 18904 available from Guilford Mills of Greensboro, N.C., USA. Other examples are available from the 3M Company of St. Paul, Minn., USA under the trade designation KLT.

An inexpensive female fastening material and a method of making the same is described in U.S. Pat. No. 5,032,122, entitled "Loop Fastening Material For Fastening Device and Method of Making Same" issued to Noel et al., Jul. 16, 1991. Another example is described in U.S. Pat. No. 5,326,612 entitled "Nonwoven Female Component for Refastenable Fastening Device and Method of Making the Same" issued to David J. K. Goulait on Jul. 5, 1994. Yet another example is described in U.S. Pat. No. 5,595,567, entitled "Nonwoven Female Component For Refastenable Fastening Device" issued Jan. 21, 1997 in the name of Willie F. King, et al. Still another example is described in U.S. Pat. No. 5,624,427 entitled "Female Component For Refastenable Fastening Device" issued Apr. 29, 1997 in the names of Carl L. Bergman, et al. Each of these patent documents is hereby incorporated by reference.

The overall thickness 316 of the female fastening material 310 is measured as described herein, in the section entitled Test Method for Measuring Thickness of a Fibrous Material. In various embodiments, the overall thickness 316 can be 1-1000 micrometers, or any integer value for micrometers between 1 and 1000, or any range formed by any of these values. As examples, the overall thickness can be 350, 500, or 650 micrometers or any range formed by any of these values.

The basis weight of the female fastening material 310 can be 10-100 grams per square meter, or any integer value for grams per square meter between 10 and 100, or any range formed by any of these values.

Figure 3B:
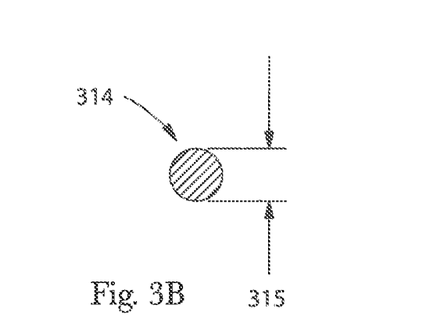
FIG. 3B is an enlarged cross-sectional view of a fiber from the female fastening material of FIG. 3A.

FIG. 3B is a further enlarged cross-sectional view of a fiber 314 from the female fastening material 310 of FIG. 3A. The fiber 314 has an overall fiber cross-sectional dimension 315. Since the shape of the fiber 314 is round, the overall cross-sectional shape of the fiber 314 is circular, and the overall fiber cross-sectional dimension 315 is the diameter of the circular overall cross-sectional shape of the fiber 314. For fibers with non-circular cross-sections, the overall fiber cross-sectional dimension is the largest distance measured linearly across the cross-section of the fiber. The overall fiber cross-sectional dimension of a fiber can be determined by making measurements on an enlarged image of the fiber, taken with equipment, at high magnification. For example, a Scanning Electron Microscope can be used.

The female fastening material 310 can include fibers of various sizes and shapes. For example, some or all of fibers in the female fastening material 310 can have an overall cross-sectional dimension of 5-150 micrometers, or any integer value for micrometers between 5 and 150 micrometers, or any range formed by any of these values. As examples, the overall thickness can be less than 25 micrometers, less than 20 micrometers, or less than 15 micrometers or any range formed by any of these values. Also as an example, some or all of the fibers in the female fastening material 310 can have an overall cross-sectional shape that is circular, oval, squarish, rectangular, triangular, star-shaped, multi-lobal, or any other shape known in the art, or combinations of any of these. As an example, a fibrous material used as a female fastening material in a hook and loop fastening system, can be a nonwoven material made from bicomponent fibers, having an overall cross-sectional dimension of 17 micrometers and an overall cross-sectional shape that is round.

Figure 4:
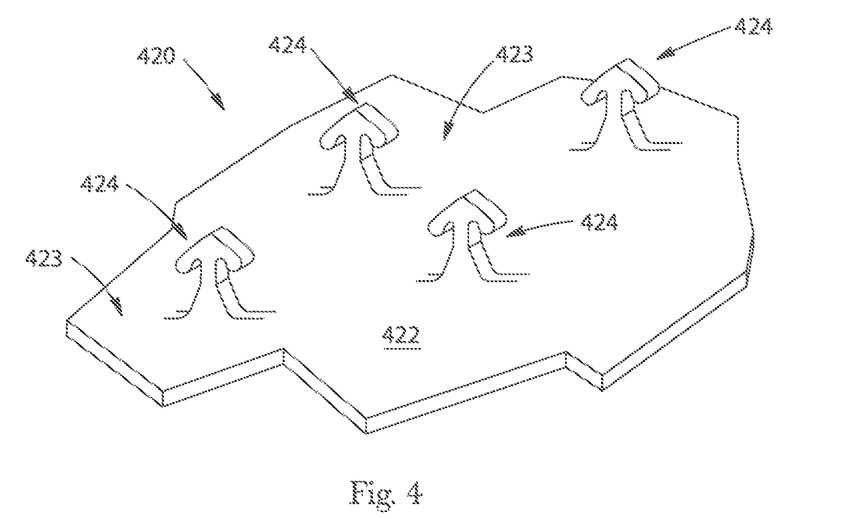
FIG. 4 is an enlarged isometric view of a portion of a male fastening material.

FIG. 4 is an enlarged isometric view of a portion of a male fastening material 420. In FIG. 4, the portion is shown as broken away from a larger piece of material. The male fastening material 420 includes a plurality of bidirectional micro-sized hooks 424 disposed on a substrate 422 that has an overall planar shape. Each of the hooks 424 can be configured in the same way as the hook 530 of FIGS. 5A-5D, including any alternative embodiments. Alternatively the male fastening material 420 can also include one or more hooks configured in other ways. In the embodiment of FIG. 4, the hooks 424 and the substrate 422 are made from the same material, and the hooks 424 are a unified part of the substrate 422. The male fastening material 420 can be made from a wide variety of shapable and/or formable materials, including any of the natural or synthetic materials recited herein and/or any other suitable material suitable known in the art, in any workable combination, along with any additives or processing aids known in the art. As a particular example, the male fastening material 420 can be made from various renewable materials, including bioplastics derived from renewable biomass sources such as sugars, starches, cellulose, biopolymers, etc. In various alternate embodiments, the hooks and the substrate may be formed separately, or made from different materials.

The hooks 424 can be distributed across the male fastening material 420 in various patterns and hook densities. For example, the hooks 424 can be arranged in rows and/or columns, or any other arrangement of hooks known in the art. In various embodiments, the male fastening material can have a hook density of 10-1,000 hooks per square centimeter, or any integer number of hooks between 10 and 1,000, or any range formed by any of these values.

Following are examples of male fastening materials suitable for use in a hook and loop fastening system. A male fastening material can include hooks having any shape such as a "J" shape, a "T" shape, or a mushroom shape, or any other shape known in the art. Exemplary male fastening materials are available from Aplix, Inc. of Charlotte, N.C., USA under the trade designation 960, 957, and 942. Other male fastening materials are available from the 3M Company of St. Paul, Minn., USA under the trade designations CS200, CS300, MC5, and MC6. Still other male fastening materials are described in U.S. Pat. No. 5,058,247 entitled "Mechanical Fastening Prong" issued to Thomas Oct. 22, 1991, which is hereby incorporated by reference.

The male fastening material 420 and the hooks 424 thereon can be made by any suitable process known in the art. For example, the male fastening material can be made by casting, molding, profile extrusion, or microreplication. Further, the male fastening material can be made by using any process described in any of the following U.S. Pat. Nos. 3,192,589; 3,138,841; 3,266,113; 3,408,705; 3,557,413; 3,594,863; 3,594,865; 3,718,725; 3,762,000; 4,001,366; 4,056,593; 4,189,809; 4,290,174; 4,454,183; 4,894,060; 5,077,870; 5,315,740; 5,607,635; 5,679,302; 5,879,604; 5,845,375; 6,054,091; 6,206,679; 6,209,177; 6,248,419; 6,357,088; 6,481,063; 6,484,371; 6,526,633; 6,635,212; 6,660,202; 6,728,998; 6,737,147; 6,869,554; RE38,652; 6,982,055; 7,014,906; 7,048,818; 7,032,278; 7,052,636; 7,052,638; 7,067,185; 7,172,008; 7,182,992; 7,185,401; 7,188,396; and 7,516,524, each of which is hereby incorporated by reference.

In another alternate embodiment, the hooks may be joined together to form a male fastening material without a substrate that has an overall planar shape. For example, a male fastening material can be made from a plurality of hooks that are disposed on one or more strips of material, or disposed on one or more strands of material, or hooks that are joined together to form one or more strips or one or more strands of material, or hooks that are connected to one or more other common elements, in any manner known in the art.

Figure 5A:
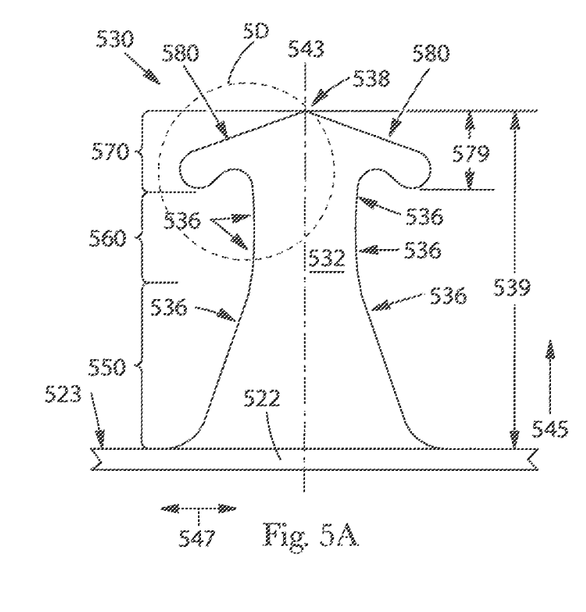
FIG. 5A is an enlarged view of a front of a bidirectional micro-sized hook disposed on a top surface of a substrate of a male fastening material.

FIG. 5A is an enlarged view of a front 532 of a bidirectional micro-sized hook 530 disposed on a top surface 523 of a portion of a substrate 522 of a male fastening material. In FIG. 5A, the portion of the substrate 522 is shown as broken away from a larger piece of material. The hook 530 is bidirectional since the cap 570 has two arms 580, extending from opposite sides 536 of the hook 530. The sides 536 of the hook are the outside portions of the hook 530, between a front 532 of the hook 530 and a back 534 of the hook 530. While the hook 530 is a bidirectional hook, it is contemplated that any of the structures, features, sizes, or dimensions of the hook 530 can be similarly applied to a unidirectional hook (one arm configured to hook in one direction) or to a multi-directional hook (more than two arms, with each arm configured to hook in a different direction).

In the embodiment of FIG. 5A, both of the arms 580 of the hook 530 are configured in the same way. However, it is also contemplated that any of the structures, features, sizes, or dimensions of an arm 580 of the hook 530 can be applied to one arm of a bidirectional hook, while the other arm can be configured in a different way. Further, it is contemplated that any of the structures, features, sizes, or dimensions of an arm 580 of the hook 530 can be applied to two or more arms of a multi-directional hook, while one or more other arms on that hook can be configured in one or more different ways.

The hook 530 includes a base 550, a stem 560, and a cap 570. The hook 530 also has sides 536. The hook 530 projects out from the substrate 522 in an upward direction 545, which is perpendicular to the substrate 522. The hook 530 also has a width direction 547. The width direction 547 is parallel to the overall planar shape of the substrate 522 and parallel to the largest linear dimension measured across the cap 570. In the embodiment of FIG. 5A, the width direction 547 is also parallel to the front 532 of the hook 530 and perpendicular to the sides 536. The hook 530 also has a thickness direction 541, which is parallel to the substrate 522 and perpendicular to the width direction 547. The thickness direction 541 is perpendicular to the page in FIG. 5A, so the thickness direction 541 is shown in FIGS. 5B and 5C.

The base 550 is attached to the substrate 522, the stem 560 is attached to the base 550, and the cap 570 is attached to the stem 560. The cap 570 has an overall cap height 579, which is measured as described in connection with FIG. 5D. The hook 530 also has an overall hook height 539 measured linearly in the upward direction 545 from the top surface 523 of the substrate 522 to a highest point on the outer surface of the hook 530 (farthest away from the top surface 523 of the substrate 522). In the embodiment of FIG. 5A, a peak 538 of the cap 570 is the highest point on the outer surface of the hook 530. The hook 530 also has a central axis 543, which passes through the center of the hook. In the embodiment of FIG. 5A, the central axis 543 is aligned with the upward direction 545, however, in various embodiments, the central axis 543 may not be perpendicular with respect to the substrate 522; that is the hook may be tipped in the width direction 547 and/or the thickness direction 541. Also, in various embodiments the cap 570 may not have a peak, but may have a rounded top, or a flat top, or a recessed top, or any other shape known in the art or combinations of any of these.

When the hook 530 is used on a male fastening material of a fastening system, and the fastening system uses a fibrous material as the female fastening material, the overall hook height 539 can be sized to the overall thickness of the fibrous material, such as the overall thickness 316 of the female fastening material 310. The overall hook height 539 can be 33-200% of the overall thickness of the fibrous material, or any integer value of percentage between 33% and 200% of the overall thickness of the fibrous material, or any range formed by any of these values. As examples, the overall hook height 539 can be 33%, 50%, 100%, 150%, or 200% of the overall thickness of the fibrous material, or any range formed by any of these values. While not wishing to be bound by this theory, it is believed that, selecting an overall hook height 539 based on the overall thickness of the fibrous material, as described above, allows the hook 530 to penetrate the fibrous material to a significant depth, which increases the likelihood that the hook 530 can encounter fibers to be captured by the hook 530.

Figure 5B:
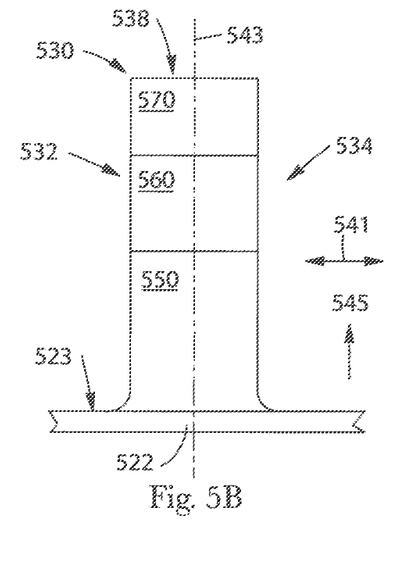
FIG. 5B is an enlarged side view of the hook of FIG. 5A disposed on the top surface of the substrate.
Figure 5C:
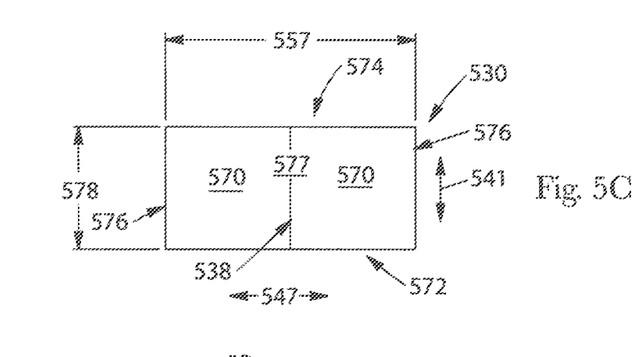
FIG. 5C is an enlarged top view of the hook of FIG. 5A.

FIG. 5B is an enlarged side view of the hook 530 of FIG. 5A disposed on the top surface 523 of a portion of the substrate 522. In FIG. 5B, the portion of the substrate 522 is shown as broken away from a larger piece of material. The hook 530 has the front 532 and the back 534, each of which is substantially flat, however in various embodiments the front 532 and/or the back 534 may not be flat. FIG. 5B illustrates the thickness direction 541, which is parallel to the substrate 522 and perpendicular to the width direction 547. In the embodiment of FIG. 5A, the thickness direction 541 is also perpendicular to the front 532 and the back 534 of the hook 530.

FIG. 5C is an enlarged top view of the hook of FIG. 5A. The top view of the hook 530 shows a to view of the cap 570. The cap 570 has a front edge 572, a back edge 574, and side edges 576. In the embodiment of FIG. 5A, each of these edges is substantially flat, however in various embodiments any of these edges may not be flat. For example, any of the edges of the cap 570 can be curved inward or outward to form a concave or convex shape, or can have other variations in its geometry. The front edge 572 and the back edge 574 are parallel with the width direction 547 and with each other, however in various embodiments these edges may not be parallel. The side edges 576 are parallel with the thickness direction 541 and with each other, however in various embodiments these edges may not be parallel. The front edge 572 and the hack edge 574 have the same overall width 557, which is measured linearly in the width direction 547, however in various embodiments the overall widths of the from and back edges may differ. The side edges 576 have the same overall thickness 578, which is measured linearly in the thickness direction 541, however in various embodiments the overall widths of the side edges may differ.

The front edge 572, the back edge 574, and the side edges 576 together, when viewed from above the peak 538 of the hook 530, define a vertical engagement effective area 577. That is, the vertical engagement effective area 577 is an area measured in a plane that is parallel with the substrate 522 and above the highest point of the hook 530, wherein the area is defined by the perimeter of the cap 570. In the embodiment of FIG. 5C, the perimeter of the cap 570 is formed by the front edge 572, the back edge 574, and the side edges 576, so these edges define the vertical engagement effective area 577. In the embodiment of FIG. 5C, the vertical effective engagement area 577 has an overall shape that is rectangular, however, in various embodiments, the overall shape may vary, based on the size and shape of the edges.

The vertical effective engagement area 577 has a width-to-thickness aspect ratio, which is defined as the widest overall width of the vertical engagement effective area 577 divided by the thickest overall thickness of the vertical engagement effective area 577. The width-to-thickness aspect ratio can be 1-2, or any value in increments of 0.01 between 1 and 2, or any range formed by any of these values. As examples, the width-to-thickness aspect ratio can be 1.2, 1.3, 1.6, 1.8, or 1.9, or any range formed by any of these values. In the embodiment of FIG. 5C, the vertical effective engagement area 577 has a width-to-thickness aspect ratio, which is the overall width 557 divided by the overall thickness 578. While not wishing to be bound by this theory, it is believed that, selecting these aspect ratios for the vertical effective engagement area 577, as described above, provides the cap 570 of the hook 530 with an overall shape that is less elongated so as to more easily fit into openings (between fibers) in the fibrous material, which increases the likelihood that the hook 530 can penetrate the fibrous material.

The size of the vertical effective engagement area 577 can be 40,000-120,000 square micrometers, or any value in increments of 5,000 square micrometers between 40,000 and 120,000 square micrometers, or any range formed by any of these values. As examples, the vertical effective engagement area 577 can be 40,000, 50,000, 60,000, 90,000, 100,000, or 120,000 square micrometers, or any range formed by any of these values. While not wishing to be bound by this theory, it is believed that, selecting these area dimensions for the vertical effective engagement area 577, as described above, provides the cap 570 of the hook 530 with an overall size that is small enough to easily fit into openings (between fibers) in the fibrous material, which increases the likelihood that the hook 530 can penetrate the fibrous material.

Figure 5D:
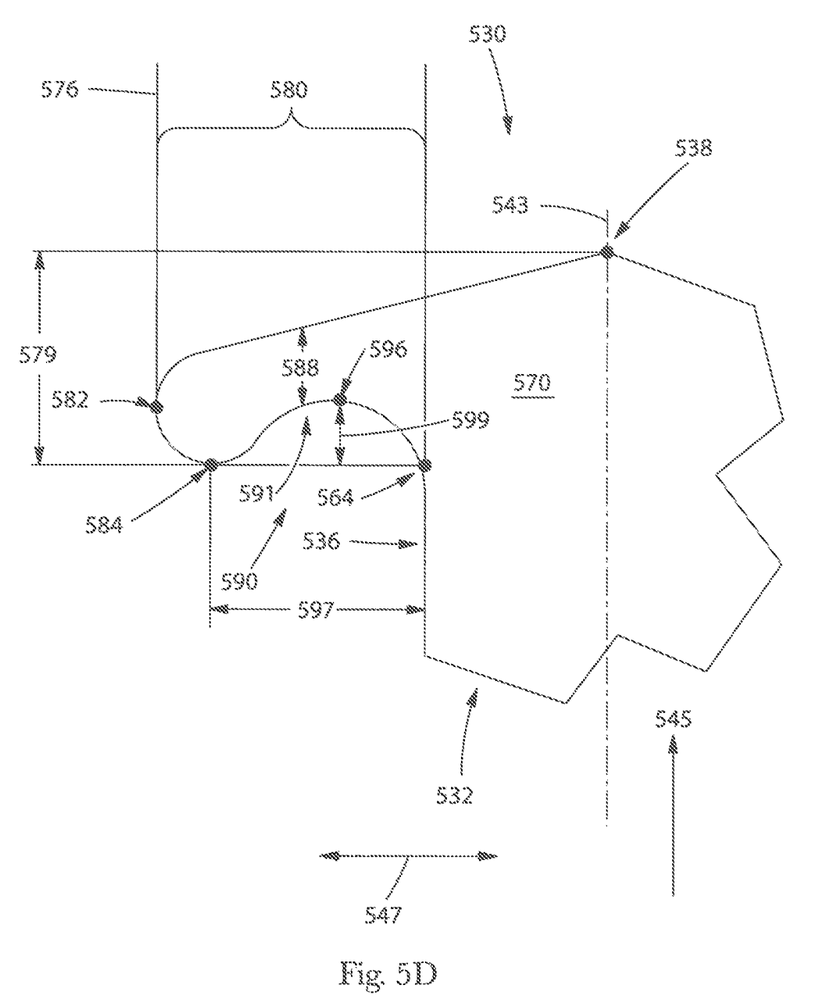
FIG. 5D is a further enlarged view of a portion of a front of the hook of FIG. 5A.

FIG. 5D is a further enlarged view of a portion of the front 532 of the hook 530 of FIG. 5A. In FIG. 5D, the portion is shown as broken away from the rest of the hook 530. FIG. 5D shows a portion of the cap 570. The portion of the cap 570 shown in FIG. 5D includes the arm 580, which extends outward from the side 536.

The structures and dimensions of the arm 580 are defined with respect to several points of reference. One reference point is a farthest point 582 on the arm 580. The farthest point 582 is a point on the arm 580 that is farthest outward from the side 536 of the hook. In FIG. 5D, the farthest point 582 is also the point on the side edge 576 of the cap 570 that is farthest away from the central axis 543. Another reference point is a lowest point 584 on an outboard end of the arm 580. The lowest point 584 is a point on the outboard end of the arm 580 (the portion of the arm 580 that is not disposed near the side 536) that is closest to the to surface 523 of the substrate 522. Still another reference point is the side point 564. The side point 564 is a point on the side 536 of the hook 530. The specific location of the side point 564 is defined by a reference plane that is parallel to the substrate 522. The reference plane passes through the lowest point 584 on the aim 580. The side point 564 is a point in the reference plane and on the side 536 of the hook that is closest to the lowest point 584.

The arm 580 begins at the side point 564. The portion of the hook 530 that is attached above the side point 564 and that is disposed outboard from the side point 564 is defined as the arm 580. The arm 580 extends from the side 536, in the width direction 547, to the farthest point 582 on the arm 580. If a hook does not include a portion that is attached above a side point and that is disposed outboard from a side point, then, for purposes of the present disclosure, the hook does not include an arm.

The cap 570 has an overall cap height 579 measured linearly in the upward direction 545 from the lowest point 584 to the highest height of the cap 570, which is the peak 538 of the cap 570 in FIG. 5D.

When the hook 530 is used on a male fastening material of a fastening system, and the fastening system uses a fibrous material as the female fastening material, the overall cap height 579 can be sized to the overall thickness of the fibrous material, such as the overall thickness 316 of the female fastening material 310. The overall cap height 579 can be 1-33% of the overall thickness of the fibrous material, or any integer value of percentage between 1% and 33% of the thickness of the overall thickness of the fibrous material, or any range formed by any of these values. As examples, the overall cap height 579 can be less than or equal to 20% or less than or equal to 25% of the overall thickness of the fibrous material. While not wishing to be bound by this theory, it is believed that, selecting these relative dimensions for the overall cap height 579, as described above, provides the cap 570 of the hook 530 with an overall size that is short enough such that there is a large open space between the lowest point 584 on the arm 580 and the top surface 523 of the substrate 522, which allows relatively more fibers to fit under the arm 580 and increases the likelihood that fibers will be captured by the hook 530.

Also, the overall cap height 579 can be sized to the overall fiber cross-sectional dimension of the fibrous material, such as the overall fiber cross-sectional dimension 315 of the fiber 314 of the female fastening material 310. The overall cap height 579 can be 1-8 times the overall fiber cross-sectional dimension, or any integer value between 1 and 8 times the overall fiber cross-sectional dimension, or any range formed by any of these values. As examples, the overall cap height 579 can be less than or equal to 6 times or less than or equal to 7 times the overall fiber cross-sectional dimension. While not wishing to be bound by this theory, it is believed that, selecting these relative dimensions for the overall cap height 579, as described above, provides the cap 570 of the hook 530 with an overall size that is short enough such that the side of the cap 570 is less likely to interfere with fibers, as the hook 530 moves through the fibrous material.

Further, the overall cap height 579 can be sized to a particular dimension. The overall cap height 579 can be 5-120 micrometers, or any value in increments of 5 micrometers between 5 and 120 micrometers, or any range formed by any of these values. As examples, the overall cap height 579 can be less than or equal to 80 micrometers or less than or equal to 100 micrometers. While not wishing to be bound by this theory, it is believed that, selecting these particular dimensions for the overall cap height 579, as described above, provides the cap 570 of the hook 530 with an overall size that is short enough such that there is a large open space between the lowest point 584 on the arm 580 and the top surface 523 of the substrate 522, which allows relatively more fibers to fit under the arm 580 and increases the likelihood that fibers will be captured by the hook 530.

The arm 580 has an underside 590, which is the bottom part of the arm 580 that is facing somewhat downward, toward the top surface 523 of the substrate 522. In various embodiments, an arm of a hook may or may not include a recessed portion. If the outer surface of the underside of an arm includes a point that is farther away from the top surface of the substrate than the lowest point on the arm, then the arm includes a recessed portion. In the embodiment of FIG. 5A, since the underside 590 of the arm 580 includes a number of points that are farther away from the top surface 523 of the substrate 522 than the lowest point 584 on the arm 580, the arm 580 includes a recessed portion 591.

If the outer surface of the underside of an arm does not include a point that is farther away from the top surface of the substrate than the lowest point on the arm, then the arm does not include a recessed portion. For example, a hook can include an arm with an underside that is parallel to the top surface of the substrate to which the hook is attached. In this example, the hook includes an arm, but the arm does not include a recessed portion.

The recessed portion 591 has an overall recessed width 597 measured linearly in the width direction 547 from the lowest point 584 on the arm 580 (as described above) to the side point 564. When the hook 530 is used on a male fastening material of a fastening system, and the fastening system uses a fibrous material as the female fastening material, the overall recessed width 597 can be sized to the overall fiber cross-sectional dimension of the fibrous material, such as the overall fiber cross-sectional dimension 315 of the fiber 314 of the female fastening material 310. The overall recessed width 597 can be 200-500% of the overall fiber cross-sectional dimension, or any integer value, of percentage between 200% and 500% of the overall fiber cross-sectional dimension, or any range formed by any of these values. As examples, the overall recessed width 597 can be 200%, 300%, 400%, or 500% of the overall fiber cross-sectional dimension, or any range formed by any of these values. While not wishing to be bound by this theory, it is believed that, selecting these relative dimensions for the overall recessed width 597, as described above, allow two to five fibers to fit in the recessed portion 591, which increases the likelihood that fibers can be retained by the hook 530.

The recessed portion 591 has a deepest recessed depth 599 measured linearly in the upward direction 545 from the lowest point 584 on the arm 580 (as described above) to the deepest point 596 on the underside 590 of the arm 580. The deepest point 596 is the point on the outer surface of the underside 590 of the arm 580, between the lowest point 584 and the side point 564, which is farthest from the top surface 523 of the substrate 522. In the embodiment of FIG. 5D, the recessed portion 591 is smooth and continuously curved. However, in various embodiments a recessed portion can have a surface that is flat, or rough, or irregular, or curved with curves separated by one or more discontinuities.

When the hook 530 is used on a male fastening material of a fastening system, and the fastening system uses a fibrous material as the female fastening material, the deepest recessed depth 599 can be sized to the overall fiber cross-sectional dimension of the fibrous material, such as the overall fiber cross-sectional dimension 315 of the fiber 314 of the female fastening material 310. The deepest recessed depth 599 can be 40-200% of the overall fiber cross-sectional dimension, or any integer value of percentage between 40% and 200% of the overall fiber cross-sectional dimension, or any range formed by any of these values. As examples, the deepest recessed depth 599 can be 50%, 60%, 100%, or 150% of the overall fiber cross-sectional dimension, or any range formed by any of these values. While not wishing to be bound by this theory, it is believed that, selecting these relative dimensions for the deepest recessed depth 599, as described above, allows one or more fibers to fit in the recessed portion 591, and increases the likelihood that fibers will be retained by the hook 530.

The deepest recessed depth 599 can also be sized in relation to the overall cap height 579. The deepest recessed depth 599 can be 10-60% of the overall cap height 579, or any integer value of percentage between 10% and 50% of the overall cap height 579, or any range formed by any of these values. As examples, the deepest recessed depth 599 can be 10%, 20%, 50%, or 60% of the overall cap height 579, or any range formed by any of these values.

The arm 580 has a thinnest arm portion 588, when measured (in the portion of the arm that corresponds with the recessed portion 591) linearly in the upward direction 545. When the hook 530 is used on a male fastening material of a fastening system, and the fastening system uses a fibrous material as the female fastening material, the thinnest arm portion 588 can be sized to the overall fiber cross-sectional dimension of the fibrous material, such as the overall fiber cross-sectional dimension 315 of the fiber 314 of the female fastening material 310. The thinnest arm portion 588 can be 70-760% of the overall fiber cross-sectional dimension, or any integer value of percentage between 70% and 760% of the overall fiber cross-sectional dimension, or any range formed by any of these values. As examples, the thinnest arm portion 588 can be 100%, 150%, 500%, or 760% of the overall fiber cross-sectional dimension, or any range formed by any of these values.

Figure 6:
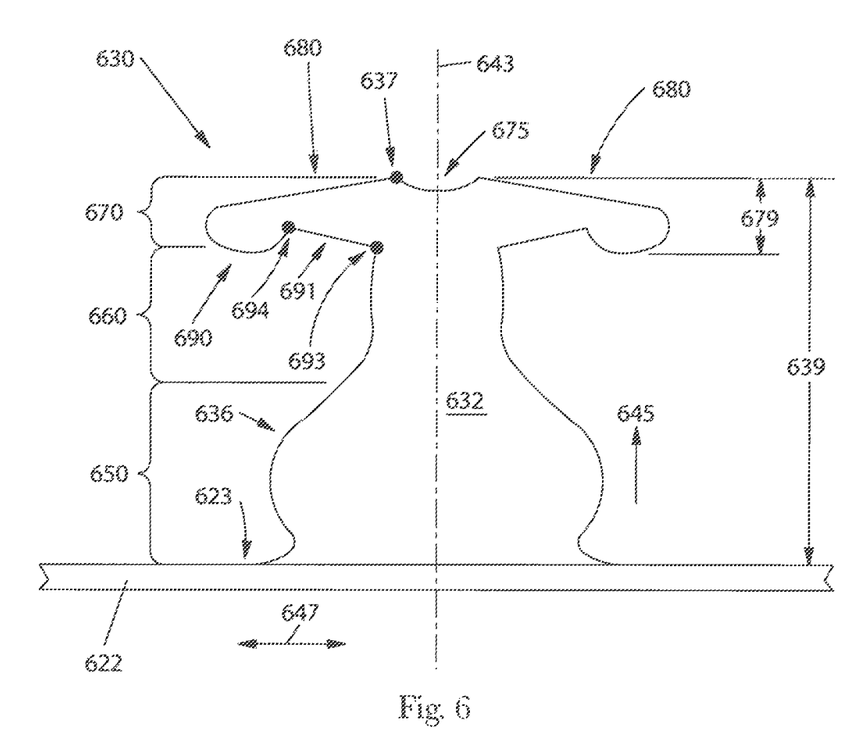
FIG. 6 is an enlarged view of a front of another bidirectional micro-sized hook disposed on a top surface of a substrate of a male fastening material.

FIG. 6 is an enlarged view of a front 632 of another bidirectional micro-sized hook 630 disposed on a top surface 623 of a substrate 622 of a male fastening material. The elements of the hook 630 are configured in the same way as the like-numbered elements of the hook 530 of FIGS. 5A-5D, except as otherwise described below. The hook 630 includes a base 650 that, when followed upward 645 from the top surface 623 of the substrate 622, narrows then widens then narrows again, up to as stem 660. The undersides 690 of arms 680 have recessed portions 691. Each recessed portion 691 is flat and angled outward from the stem 660 at point 693. The recessed portion 691 also includes a discontinuity 694 that separates the flat portion from a curve near the outboard end of the arm 680. The cap 670 of the hook 630 has a top with a recess 675. As a result, the highest point on the outer surface of the hook 630 is not a peak disposed at central axis 643, but is a point 637 at an edge of the recess 675. Part, parts, or all of the hook 630 can also be configured according to any of the alternative embodiments disclosed for the hook 530 of FIGS. 5A-5D.

Hook and loop fastening systems of the present disclosure have a female fastening material made of a fibrous material and a male fastening material having hooks configured for the fibrous material. The hooks can have an overall hook height that is sized in relation to the overall thickness of the fibrous material. The hooks can have a vertical engagement effective area with a defined size and aspect ratio. The hooks can also have an overall cap height that is sized in relation to the overall thickness of the fibrous material and/or an relation to the overall fiber cross-sectional dimension of fibers in the fibrous material. The hooks can further have arms with undersides that include recessed portions sized in relation to the overall fiber cross-sectional dimension of fibers in the fibrous material. Since the hooks of the male fastening material are configured for the loops of the fibrous material, during fastening a sufficient number of loops are effectively captured and retained by the hooks, and the male fastening material can be used to form a reliable hook and loop fastening system.

Test Method for Measuring Thickness of a Fibrous Material

In general, the overall thickness of a fibrous material is measured as follows. Thickness measurements are performed using an Ono Sokki digital caliper (GS-503 Linear Gauge Sensor with DG-3610 Digital Gauge, Ono Sokki Co, Japan or equivalent) capable of measuring to 0.01 millimeters. The circular foot's diameter is 25.4 millimeters and the applied pressure is 0.689 kilopascals. At least five test samples of the same fibrous material are measured. Before testing, each of the test samples is placed on a that surface and conditioned for 2 hours at 23±2° C. and 50±2% relative humidity. The measurements are performed under the same environmental conditions. For each test sample, three measurements are made at test sites corresponding to the longitudinal center of the test sample at 25%, 50% and 75% of the total lateral width of the test sample. For each measurement, the test sample is placed onto the caliper's anvil, with the body facing surface directed downward and with the test site centered under the foot. The foot is lowered at about 5 millimeters per second until the foot rests on the test sample. A reading from the caliper is taken after a residence time of 5 seconds and recorded to the nearest 0.01 millimeter. The foot is raised and the measurement is repeated in similar fashion at the other two test sites. The average of all measurements is reported to the nearest 0.01 millimeter. This test method can be used to measure the overall thickness of a fibrous material, such as the overall thickness 316 of the female fastening material 310 of FIG. 3A.

This test method can also be used to measure the overall thickness of a female fastening material that is used as a landing zone of a disposable wearable absorbent article, as described below. Each landing zone is considered to be a test sample. At least five test samples of the same landing zone are measured. Each landing zone is identified and then removed from the article, taking care not to significantly stretch or distort the test sample. If necessary, a cryogenic freeze spray (available as CytoFreeze, Control Company, TX or equivalent) can be used to facilitate removal of the landing zone. After removal, the landing zone is treated as a test sample and tested as described above.

Exemplary Data for Thickness of a Fibrous Material

The overall thickness of a landing zone from a current market disposable wearable absorbent article was measured. The landing zone was a nonwoven landing zone taken from six test samples of a Luv's Size 4 diaper. The landing zone was removed and the overall thickness of the landing zone was measured, as described in connection with the Test Method for Measuring Thickness of a Fibrous Material. The testing yielded overall thickness measurements (in millimeters), set forth in Table 1, provided below.

TABLE 1

| Sample | Location | | | Avg. |
| --- | --- | --- | --- | --- |
| | 25% | 50% | 75% | |
| 1 | 0.58 | 0.47 | 0.68 | 0.58 |
| 2 | 0.59 | 0.5 | 0.61 | 0.57 |
| 3 | 0.46 | 0.5 | 0.51 | 0.49 |
| 4 | 0.54 | 0.47 | 0.66 | 0.56 |
| 5 | 0.61 | 0.56 | 0.68 | 0.62 |
| 6 | 0.57 | 0.58 | 0.68 | 0.61 |
| Overall | | | | 0.57 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable wearable absorbent article having a hook and loop fastening system, the fastening system comprising:
    a female fastening material, which is a nonwoven material, having an overall thickness and having a plurality of fibers, wherein each of the fibers has an overall fiber cross-sectional dimension; and
    a male fastening material with a plurality of bidirectional micro-sized hooks, wherein:
        each of the hooks has an overall hook height that is greater than or equal to one third of the overall thickness of the female fastening material but less than or equal to twice the overall thickness of the female fastening material;
        each of the hooks includes a cap, and each of the caps has a vertical engagement effective area that:
            has an overall shape with at least two sides that are substantially parallel,
            has a width-to-thickness aspect ratio that is greater than or equal to 1 but less than or equal to 2, and
            is greater than or equal to 40,000 square micrometers but less than or equal to 120,000 square micrometers; and
        each of the caps has an overall cap height that is:
            less than or equal to one third of the thickness of the overall thickness of the female fastening material, and
            less than or equal to 120 micrometers; and
        each of the hooks has two arms, at least one of the arms having an underside, the underside including a recessed portion, the recessed portion having a deepest recessed depth that is greater than or equal to 40% of the overall fiber cross-sectional dimension and less than or equal to 200% of the overall fiber cross-sectional dimension, and the recessed portion having an overall recessed width that is greater than or equal to 200% of the overall fiber cross-sectional dimension and less than or equal to 500% of the overall fiber-cross sectional dimension, and each of the arms has a proximal end portion and a distal end portion, wherein each arm narrows in the height dimension between the proximal end portion and the distal end portion to a thinnest arm portion that is narrower in the height dimension than either the proximal end portion or the distal end portion, wherein the height of the thinnest arm portion is greater than or equal to 70% of the overall fiber cross-sectional dimension and less than or equal to 200% of the overall fiber cross-sectional dimension.

2. The disposable wearable absorbent article of claim 1, wherein each of the arms has an underside with a recessed portion.

3. The disposable wearable absorbent article of claim 1, wherein the two sides that are substantially parallel are two side edges of the cap.

4. The disposable wearable absorbent article of claim 1, wherein the overall shape of the vertical engagement effective area is rectangular.

5. The disposable wearable absorbent article of claim 1, wherein the overall hook height is greater than or equal to half of the overall thickness of the female fastening material but less than or equal to one and half times the overall thickness of the female fastening material.

6. The disposable wearable absorbent article of claim 1, wherein the overall hook height is about equal to the overall thickness of the female fastening material.

7. The disposable wearable absorbent article of claim 1, wherein the width-to-thickness aspect ratio is greater than or equal to 1.2 but less than or equal to 1.9.

8. The disposable wearable absorbent article of claim 1, wherein the width-to-thickness aspect ratio is greater than or equal to 1.3 but less than or equal to 1.8.

9. The disposable wearable absorbent article of claim 1, wherein the vertical engagement effective area is greater than or equal to 50,000 square micrometers but less than or equal to 100,000 square micrometers.

10. The disposable wearable absorbent article of claim 1, wherein the vertical engagement effective area is greater than or equal to 60,000 square micrometers but less than or equal to 90,000 square micrometers.

11. The disposable wearable absorbent article of claim 1, wherein the overall cap height is less than or equal to one fourth of the overall thickness of the female fastening material.

12. The disposable wearable absorbent article of claim 1, wherein the overall cap height is less than or equal to one fifth of the overall thickness of the female fastening material.

13. The disposable wearable absorbent article of claim 1, wherein the overall cap height is less than or equal to 100 micrometers.

14. The disposable wearable absorbent article of claim 1, wherein the overall cap height is less than or equal to 80 micrometers.

15. The disposable wearable absorbent article of claim 1, wherein the overall thickness of the female fastening material is less than or equal to 650 micrometers.

16. The disposable wearable absorbent article of claim 1, wherein the overall thickness of the female fastening material is less than or equal to 500 micrometers.

17. The disposable wearable absorbent article of claim 1, wherein the overall thickness of the female fastening material is less than or equal to 350 micrometers.

18. The disposable wearable absorbent article of claim 1, wherein the female fastening material is a spunbond nonwoven material.

19. The disposable wearable absorbent article of claim 1, including an outer cover with a fibrous outer surface, and the female fastening material is included in a landing zone disposed on the outer cover.

20. A disposable wearable absorbent article having a hook and loop fastening system, the fastening system comprising:
a female fastening material, which is a nonwoven, having a plurality of fibers, wherein each of the fibers has an overall fiber cross-sectional dimension; and
a male fastening material with a plurality of micro-sized hooks, wherein:
each of the hooks includes a cap, and each of the caps has:
a vertical engagement effective area that has an overall shape with at least two sides that are substantially parallel, and
an overall cap height that is less than or equal to eight times the overall fiber cross-sectional dimension, and
each of the hooks has an arm, with an underside, and the underside includes a recessed portion, which has a deepest recessed depth that is greater than or equal to 40% of the overall fiber cross-sectional dimension and less than or equal to 200% of the overall fiber cross-sectional dimension, and which has an overall recessed width that is greater than or equal to 200% of the overall fiber cross-sectional dimension and less than or equal to 500% of the overall fiber-cross sectional dimension, and each of the arms has a proximal end portion and a distal end portion, wherein each arm narrows in the height dimension between the proximal end portion and the distal end portion to a thinnest arm portion that is narrower in the height dimension than either the proximal end portion or the distal end portion, wherein the height of the thinnest arm portion is greater than or equal to 70% of the overall fiber cross-sectional dimension and less than or equal to 200% of the overall fiber cross-sectional dimension.

21. The disposable wearable absorbent article of claim 20, wherein the overall cap height that is less than or equal to seven times the overall fiber cross-sectional dimension.

22. The disposable wearable absorbent article of claim 20, wherein the overall cap height that is less than or equal to six times the overall fiber cross-sectional dimension.

23. The disposable wearable absorbent article of claim 20, wherein the overall fiber cross-sectional dimension is less than or equal to 25 micrometers.

24. The disposable wearable absorbent article of claim 20, wherein the overall fiber cross-sectional dimension is less than or equal to 20 micrometers.

25. The disposable wearable absorbent article of claim 20, wherein the overall fiber cross-sectional dimension is less than or equal to 15 micrometers.

26. The disposable wearable absorbent article of claim 20, wherein the two sides that are substantially parallel are two side edges of the cap.

27. The disposable wearable absorbent article of claim 20, wherein the overall shape of the vertical engagement effective area is rectangular.

28. The disposable wearable absorbent article of claim 20, wherein the overall cap height is less than or equal to 120 micrometers.

29. The disposable wearable absorbent article of claim 20, wherein the overall cap height is less than or equal to 100 micrometers.

30. The disposable wearable absorbent article of claim 20, wherein the overall cap height is less than or equal to 80 micrometers.

31. A disposable wearable absorbent article having a hook and loop fastening system, the fastening system comprising:
a female fastening material, which is a nonwoven, having a plurality of fibers, wherein each of the fibers has an overall fiber cross-sectional dimension; and
a male fastening material with a plurality of micro-sized hooks, wherein:
each of the hooks has an arm with an underside, and the underside includes a recessed portion, which has:
an overall recessed width that is greater than or equal to 200% of the overall fiber cross-sectional dimension but less than or equal to 500% of the overall fiber cross-sectional dimension, and
a deepest recessed depth that is greater than or equal to 40% of the overall fiber cross-sectional dimension but less than or equal to 200% of the overall fiber cross-sectional dimension, and
wherein each arm has a proximal end portion and a distal end portion, wherein each arm narrows in the height dimension between the proximal end portion and the distal end portion to a thinnest arm portion that is narrower in the height dimension than either the proximal end portion or the distal end portion, wherein the height of the thinnest arm portion is greater than or equal to 70% of the overall fiber cross-sectional dimension and less than or equal to 200% of the overall fiber cross-sectional dimension.

32. The disposable wearable absorbent article of claim 31, wherein the overall recessed width is greater than or equal to 200% of the overall fiber cross-sectional dimension but less than or equal to 400% of the overall fiber cross-sectional dimension.

33. The disposable wearable absorbent article of claim 31, wherein the overall recessed width is greater than or equal to 200% of the overall fiber cross-sectional dimension but less than or equal to 300% of the overall fiber cross-sectional dimension.

34. The disposable wearable absorbent article of claim 31, wherein the deepest recessed depth is greater than or equal to 50% of the overall fiber cross-sectional dimension but less than or equal to 150% of the overall fiber cross-sectional dimension.

35. The disposable wearable absorbent article of claim 31, wherein the deepest recessed depth is greater than or equal to 60% of the overall fiber cross-sectional dimension but less than or equal to 100% of the overall fiber cross-sectional dimension.

36. The disposable wearable absorbent article of claim 31, wherein the deepest recessed depth is greater than or equal to 10% of the overall cap height but less than or equal to 60% of the overall cap height.

37. The disposable wearable absorbent article of claim 31, wherein the deepest recessed depth is greater than or equal to 20% of the overall cap height but less than or equal to 50% of the overall cap height.

38. The disposable wearable absorbent article of claim 31, wherein each of the hooks is a bidirectional hook.

39. The disposable wearable absorbent article of claim 31, wherein the overall fiber cross-sectional dimension is less than or equal to 25 micrometers.

40. The disposable wearable absorbent article of claim 31, wherein the overall fiber cross-sectional dimension is less than or equal to 20 micrometers.

41. The disposable wearable absorbent article of claim 31, wherein the overall fiber cross-sectional dimension is less than or equal to 15 micrometers.

42. The disposable wearable absorbent article of claim 31, wherein the female fastening material is a spunbond nonwoven material.

43. The disposable wearable absorbent article of claim 31, including an outer cover with a fibrous outer surface, and the female fastening material is included in a landing zone disposed on the outer cover.

44. The disposable wearable absorbent article of claim 20, wherein the female fastening material is a spunbond nonwoven material.

* * * * *